(12) United States Patent  (10) Patent No.: US 6,964,508 B2
Yoneda et al.  (45) Date of Patent: Nov. 15, 2005

(54) FIBER OPTIC BUNDLE LIGHTING UNITS PROVIDING FOCUSED ILLUMINATION

(75) Inventors: Kenji Yoneda, Kyoto (JP); Shigeki Masumura, Kyoto (JP)

(73) Assignee: CCS, Inc., Kyoto (JP)

( * ) Notice: Subject to any disclaimer, the term of this patent is extended or adjusted under 35 U.S.C. 154(b) by 0 days.

(21) Appl. No.: 10/413,757

(22) Filed: Apr. 15, 2003

(65) Prior Publication Data

US 2003/0193817 A1  Oct. 16, 2003

(30) Foreign Application Priority Data

Apr. 16, 2002 (JP) ............................ P2002-113979
Jul. 16, 2002 (JP) ............................ P2002-207061

(51) Int. Cl.$^7$ .............................................. F21V 7/04
(52) U.S. Cl. ...................... 362/555; 362/269; 362/575
(58) Field of Search .............................. 362/551, 572, 362/575, 555, 556, 568, 583, 588, 584, 800, 362/268, 269; 356/73, 318, 257.1, 237, 316, 356/237.1

(56) References Cited

U.S. PATENT DOCUMENTS

| | | | | |
|---|---|---|---|---|
| 3,971,621 A | * | 7/1976 | Albrecht-Buehler | 359/390 |
| 5,051,872 A | * | 9/1991 | Anderson | 362/558 |
| 5,102,227 A | * | 4/1992 | Zwirner et al. | 362/31 |
| 5,430,620 A | * | 7/1995 | Li et al. | 362/572 |
| 5,810,463 A | * | 9/1998 | Kawahara et al. | 362/31 |
| 6,042,256 A | * | 3/2000 | Gothard | 362/558 |
| 6,069,689 A | * | 5/2000 | Zeng et al. | 356/73 |
| 6,290,382 B1 | * | 9/2001 | Bourn et al. | 362/554 |
| 6,538,729 B2 | | 3/2003 | Yoneda | 356/237.2 |
| 6,601,985 B1 | * | 8/2003 | Jesurun et al. | 362/572 |

FOREIGN PATENT DOCUMENTS

| | | |
|---|---|---|
| EP | 0 935 135 | 8/1999 |
| WO | WO 00/01984 | 10/2000 |
| WO | WO 01/98760 | 12/2001 |

* cited by examiner

Primary Examiner—John Anthony Ward

(57) ABSTRACT

An efficient lighting unit with improvements in ease of moving its head, reliability and the like is provided. The lighting unit includes: heads 6A and 6B defining illuminating apertures 6Aa and 6Ba, respectively, for directing light to an object W to be illuminated, the heads 6A and 6B being supported by a movable support member 1; LED light source devices 5A and 5B mounted at the movable support member 1 for emitting light when supplied with electric power from an electric power source 3 disposed separately from the movable support member 1 through an electric cable 4; and flexible optical fibers 7A and 7B for guiding light from the LED light source devices 5A and 5B to the respective illuminating apertures 6Aa and 6Ba of the heads 6A and 6B.

13 Claims, 18 Drawing Sheets

FIBER OPTIC BUNDLE LIGHTING UNITS PROVIDING FOCUSED ILLUMINATION

BACKGROUND OF THE INVENTION

1. Field of the Invention

The present invention relates to lighting units for use in inspecting products for their outward appearances, flaws or finished conditions, or in position detection or like applications.

2. Description of the Related Art

Hitherto, halogen lamps are known as representatives of light sources for use in lighting units of this type. Since such a halogen lamp has limited freedom in selection of a suitable place to which the halogen lamp is to be installed due to its bulkiness and since it is difficult to condense light from the halogen lamp, it has been a conventional practice to illuminate a work not directly from a halogen lamp but indirectly by guiding light from the halogen lamp through an optical fiber to a head attached to the front end of the optical fiber, as described in Japanese Patent Laid-Open Gazette No. HEI 5-248820. Such an optical fiber is used because it has flexibility and can be cut to a desired length and hence allows the halogen lamp to be freely located at an easy-to-install place even if the place is, for example, remote from the lighting site.

A lighting unit for illuminating works that are constantly at non-fixed positions such as those inaccurately positioned on and fed one after another by a conveyor unit, needs to have a function allowing the head having an illuminating aperture to move frequently in accordance with the position of each work.

Of course, the optical fiber used in such a lighting unit moves with frequent movements of the illuminating aperture. Since such an optical fiber has flexibility, it has heretofore been considered that such a lighting unit can accommodate well to applications where the head needs to move as described above.

Actually, however, particularly where a relatively long (for example 2 or 3 meters or longer) optical fiber is used, it is likely that an up-sized driving mechanism is needed for moving the head while causing the associated optical fiber to accompany the head or that movement of or position control over the head becomes difficult, because generally an optical fiber is relatively bulky and heavy as compared to electric wires or the like.

Further, since optical fibers are less flexible than electric wires, they are likely to be damaged in a relatively short time by frequent bending and moving, which may result in problems in respect of the reliability, lifetime and the like of the lighting unit.

It is possible to use an LED, which recently has been attracting attention as a substitute for a halogen lamp, as a light source. However, where a multiplicity of LEDs are directly fitted to a head without using an optical fiber, a problems arises that downsizing of the head and light condensing are difficult. For example, when a very small object, such as a component mounted on a printed circuit board, is to be illuminated, such a head fitted directly with LEDs has a relatively large minimum focal diameter and hence illuminates the object as well as unwanted portions, which results in inefficient lighting.

The present invention, which is not made until the conventional concept of moving the head by utilizing the flexibility and the length adjustability of an optical fiber has been abandoned completely, intends to solve the foregoing problems at a time by taking advantages of the lightness, compactness and the like of an LED light source device as well as the advantage of an optical fiber head in its possibility to reduce the size thereof.

SUMMARY OF THE INVENTION

According to one aspect of the present invention, there is provided a lighting unit comprising: a head defining an illuminating aperture for directing light to an object to be illuminated, the head being supported by a movable support member; an LED light source device mounted at the movable support member for emitting light when electric power is supplied thereto from an electric power source disposed separately from the movable support member through an electric cable; and at least one flexible optical fiber for guiding light from the LED light source device to the illuminating aperture of the head.

With the lighting unit of the construction described above, the weight and size of the LED light source device can be reduced easily and, therefore, the LED light source device thus reduced in weight and size, though mounted at the movable support member, can hardly exert influence on the driving of the movable support member, hence, of the head.

If the head is fixedly supported by the movable support to maintain the relative positional relation between the LED light source device and the head, it is possible to reduce the burden to be imposed on the optical fiber, thereby to eliminate the influence of such a burden on the reliability, lifetime and the like of the optical fiber. Of course, the head may be mounted at the movable support member so as to be slightly movable or slowly movable relative to the movable support member unless such movement affects the reliability, lifetime and the like of the optical fiber.

Since the head is connected to the optical fiber and is separate from the LED light source device, it is possible to make the size of the head very small as well as to condense light onto a small area. Further, since the light source can be spaced apart to a certain extent from the object to be illuminated or from an image pick-up device for imaging the object, it is also possible to prevent the object or the image pick-up device from being affected by heat generated from the light source.

The LED light source device may be supplied with electric power either from a battery provided in or incident to the lighting unit or from an electric power source disposed separately from the movable support member through an electric cable. With the former arrangement, the lighting unit can be rendered cableless. Alternatively, though the latter arrangement requires an electric cable, the electric cable is far superior to an optical fiber in flexibility, durability, price and the like. Therefore, the latter arrangement is capable of highly reliably driving the movable support member and the head with a very light burden on the electric cable as compared to the burden that has been conventionally imposed on an optical fiber when the optical fiber is moved with the movement of the head. An arrangement for supplying electric power from an image pick-up device may also be conceived.

In the present invention, the light source device may be disposed adjacent the illuminating aperture to shorten the optical fiber (to 1 m or less for example), thereby reducing the weight of the optical fiber. With this feature, the head can be driven smoothly even if it is movably mounted at the movable support member. In this case, it is preferred that the head be mounted at the movable support member so as to be slightly movable or slowly movable relative to the movable support member unless such movement affects the reliability, lifetime and the like of the optical fiber.

For obtaining an improved light-condensing characteristic, the optical fiber is preferably fitted with a lens at a front end thereof on a head side.

One desirable form of the electric cable is a robot cable.

According to another aspect of the present invention, there is provided a lighting unit for use in line inspection, which is developed from the technical concept described above.

The lighting unit for use in line inspection comprises: a fiber cable in which a multiplicity of optical fibers extending from light-receiving ends thereof facing a light-emitting surface of an LED light source device into a head unit are bundled and accommodated; an optical fiber aligning and holding member holding light-emitting ends of the respective optical fibers as aligned in a horizontal row by releasing the bundled state of front end portions of the multiplicity of optical fibers introduced into the head unit from a rear end thereof within the head unit and sequentially juxtaposing the front end portions with each other in a same plane; and a pair of lenses fitted at a front end portion of the head unit, the pair of lenses consisting of a first lens for turning a band of light emitted from the horizontal row of the light-emitting ends of the optical fibers into substantially parallel rays of light and a second lens for causing light outgoing from the first lens to converge into line light consisting of an elongated band of light.

In the above-described construction, the optical fiber aligning and holding member may be mounted at the head unit so as to be position-adjustable in fore-and-aft directions, thereby adjusting the focusing position of line light. Thus, the lighting unit is capable of lighting in accordance with objects to be illuminated.

The lighting unit of the above-described construction may further comprises an optical member for providing a uniform luminance distribution in a direction in which the line light extends, the optical member being disposed at the front end portion of the head unit so as to be associated with the pair of lenses.

In the above-described construction, the head unit has opposite inner wall surfaces formed with respective plane mirrors extending to cover from opposite ends of the horizontal row of the light-emitting ends of the multiplicity of optical fiber and to opposite extremities of the pair of lenses. This feature allows the opposite inner surfaces to reflect light deviated in opposite directions in a same plane outwardly of the opposite ends of the row of the light-emitting ends, thereby compensating for a loss in light quantity at opposite ends of the line light.

There is also provided a light unit comprising a plurality of lighting units as recited above with respective head units arranged in a row for forming a continuous line light illumination pattern having a length corresponding to a total width of the head units.

According to yet another aspect of the present invention, there is provided a lighting unit for use in line inspection, comprising: a fiber cable in which a multiplicity of optical fibers extending from light-receiving ends thereof facing a light-emitting surface of an LED light source device into a head unit are bundled and accommodated; an optical fiber aligning and holding member holding light-emitting ends of the respective optical fibers as aligned in a horizontal row by releasing the bundled state of front end portions of the multiplicity of optical fibers introduced into the head unit from a rear end thereof within the head unit and sequentially juxtaposing the front end portions with each other in a same plane, the optical fiber aligning and holding member being position-adjustable in fore-and-aft directions within the head unit; converging and illuminating means provided at a front end portion of the head unit for causing a band of light emitted from the horizontal row of the light-emitting ends of the optical fibers to converge into a thinner band of light at a position forward of the head unit; a lenticular screen for providing a uniform luminance distribution in a direction in which line light extends, the lenticular screen being disposed at the front end portion of the head unit so as to be associated with the converging and illuminating means; and a pair of plane mirrors formed on opposite inner wall surfaces of the head unit so as to extend to cover from opposite ends of the horizontal row of the light-emitting ends of the multiplicity of optical fibers to opposite extremities of the converging and illuminating means.

The foregoing and other objects, features and attendant advantages of the present invention will become apparent from the reading of the following detailed description in conjunction with the accompanying drawings.

BRIEF DESCRIPTION OF THE DRAWINGS

FIGS. 17(A), 17(B) and 17(C) are a plan view, a side view in section and a front end view, respectively, of a portion of interest of the head device and FIG. 17(D) is a schematic view illustrating an out-of-focus state assumed when a cylindrical lens is used.

DETAILED DESCRIPTION OF THE PREFERRED EMBODIMENTS

Figure 1:
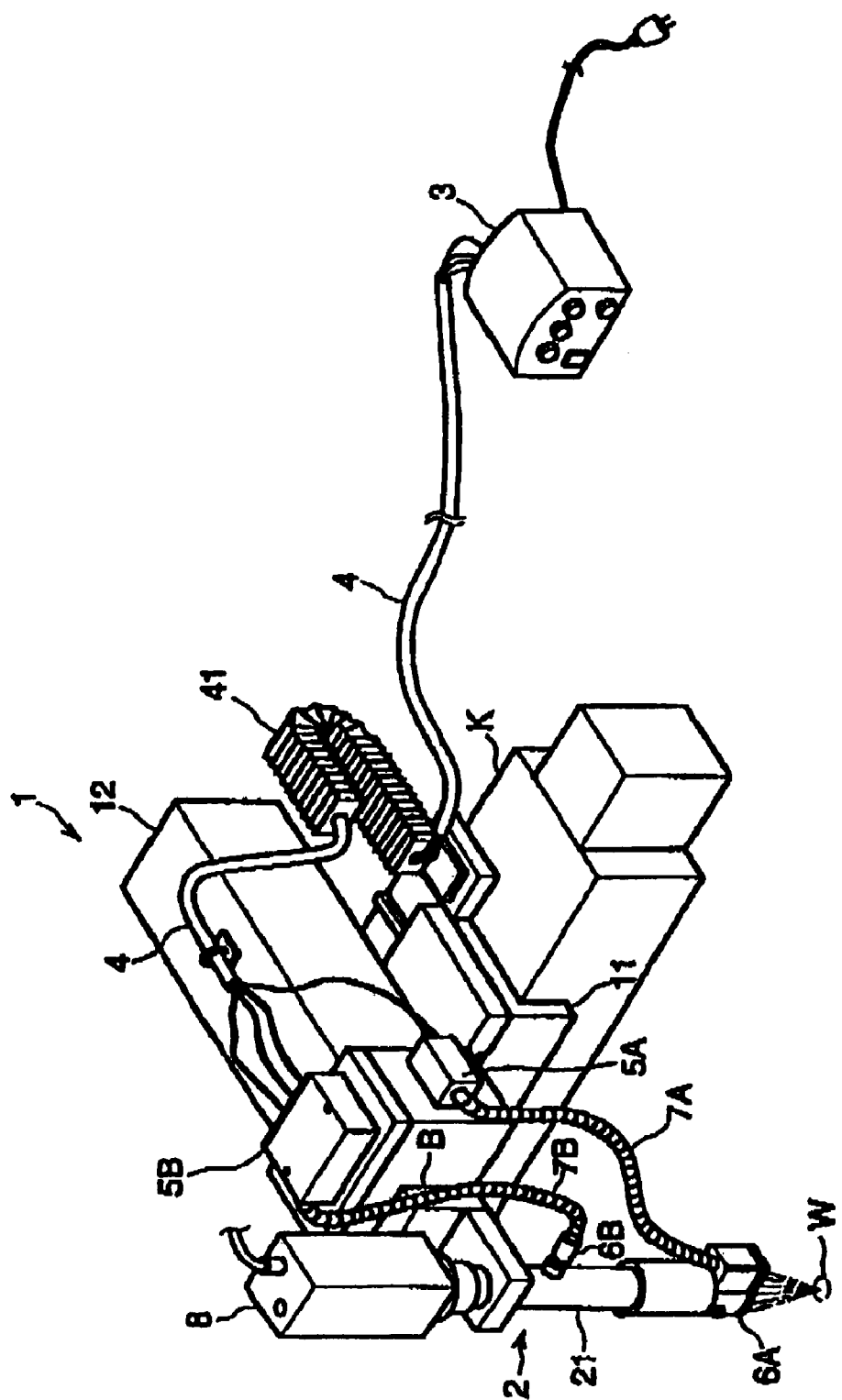
FIG. 1 is an overall perspective view of a lighting unit according to one embodiment of the present invention.

The present invention will now be described in detail with reference to the accompanying drawings wherein like reference characters designate like or corresponding parts throughout several views.

Referring to FIG. 1, there is shown a lighting unit according to one embodiment of the present invention, which utilizes an XY stage 1 as a movable support member that is biaxially movable in a horizontal plane, i.e., horizontally movable along X-axis and Y-axis. The lighting unit includes a unit body 2 supported by the XY stage 1, an electric power source 3 installed separately from the XY stage 1, LED light source devices 5A and 5B to be supplied with electric power from the electric power source 3 through a robot cable 4, heads 6A and 6B mounted on the unit body 2 and defining illuminating apertures 6Aa and 6Ba, respectively, for directing light to a work W as an object to be illuminated, optical fiber bundles 7A and 7B as light guides for guiding light from the LED light source devices 5A and 5B to the heads 6A and 6B, and an image pick-up device 8 for imaging the work W. The lighting unit is adapted to apply light outgoing from the illuminating apertures 6Aa and 6Ba onto the work W as an object to be inspected that has been conveyed to a predetermined position by a conveyor unit and inspect the outward appearance of the work W by means of the image pick-up device 8.

Description will be made of each part of the lighting unit.

The XY stage 1 comprises, for example, an X stage 11 supported for horizontal sliding along the X-axis by a stationary member K placed on the conveyor unit or the floor for example, and a Y stage 12 supported by the X stage 11 for horizontal sliding along the Y-axis. Thus, the Y stage 12 can be freely positioned in a horizontal plane by moving biaxially in the horizontal plane. Each of the stages 11 and 12 is driven to position either under remote control or automatically with use of a non-illustrated driving mechanism such as a stepping motor for example.

The unit body 2 is fixed to the XY stage 1, specifically to the Y stage 12 via a bracket B, and includes a cylindrical light path tube 21 standing vertically and accommodating therein non-illustrated optical components such as a half mirror and a lens. By driving the XY stage 1, the unit body 2 can be moved so that the light path tube 21 becomes positioned just above the work W.

The image pick-up device 8 is, for example, a CCD camera and is fixed to an upper end portion of the light path tube 21 so that its image pick-up side is oriented downward.

The electric power source 3 is a DC power source for supplying power to the LED light source devices 5A and 5B and is disposed at a predetermined location remote from the XY stage 1. The robot cable 4 extending from the electric power source 3 passes through a cable bearer 41 of a bellows configuration and reaches the LED light source devices 5A and 5B. In FIG. 1, the cable bearer 41 has one end attached to the X stage 11 and the other end attached to the Y stage 12 and functions to prevent the cable 4 from being twisted or entangled due to movement of the Y stage 12 relative to the X stage 11. It is, of course, possible to provide another cable bearer between the stationary member K and the X stage 11.

Two types of LED light source devices 5A and 5B, for example, are used in this embodiment. The LED light source device 5A comprises a single power LED 52 accommodated in an enclosure 53, while the LED light source device 5B comprises a plurality of power LEDs 52A for emitting light of different colors (three colors R, G and B) accommodated in an enclosure 53A.

Figure 2:
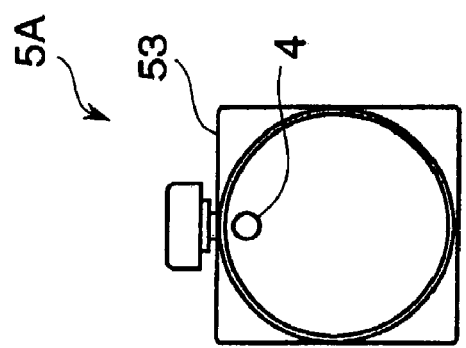
FIGS. 2(A) and 2(B) are a vertical sectional view and a rear view, respectively, of a first LED light source device in the same embodiment.
Figure 2:
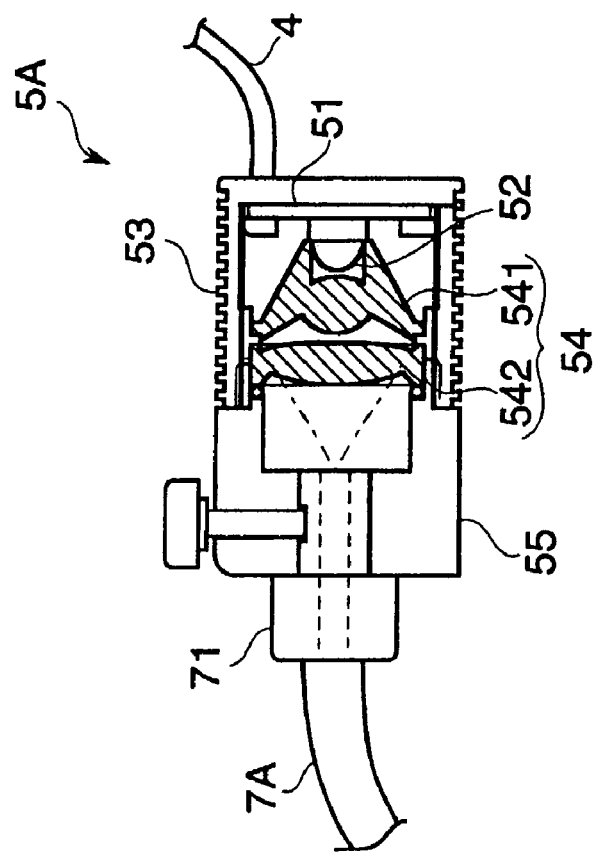

As shown in FIG. 2, one LED light source device 5A includes the LED 52 mounted on a substrate 51, a lens mechanism 54 for condensing light emitted from the LED 52, and an optical output connector 55 for guiding light outgoing from a light-condensing portion 54a of the lens mechanism 54 to the optical fiber bundle 7A. The LED 52 is a bare chip of a surface emitting type, and the substrate 51 supporting the LED 52 is connected to the electric cable 4 which extends from a side of the enclosure 53. The lens mechanism 54 comprises a pair of first and second lenses arranged serially and intervenes between the LED 52 and the optical output connector 55. The first lens positioned on the LED 52 side turns light emitted from the LED 52 into parallel rays of light and then the second lens condenses the parallel rays of light. In the subject embodiment, a conical lens 541 and a convex condenser lens 542 are arranged to face each other. The light-emitting surface of the LED 52 is embedded in a base end portion of the first lens 541. A base end portion of the second lens 542 serves as the light-condensing portion 54a for causing light emitted from the LED 52 to converge.

Figure 3:
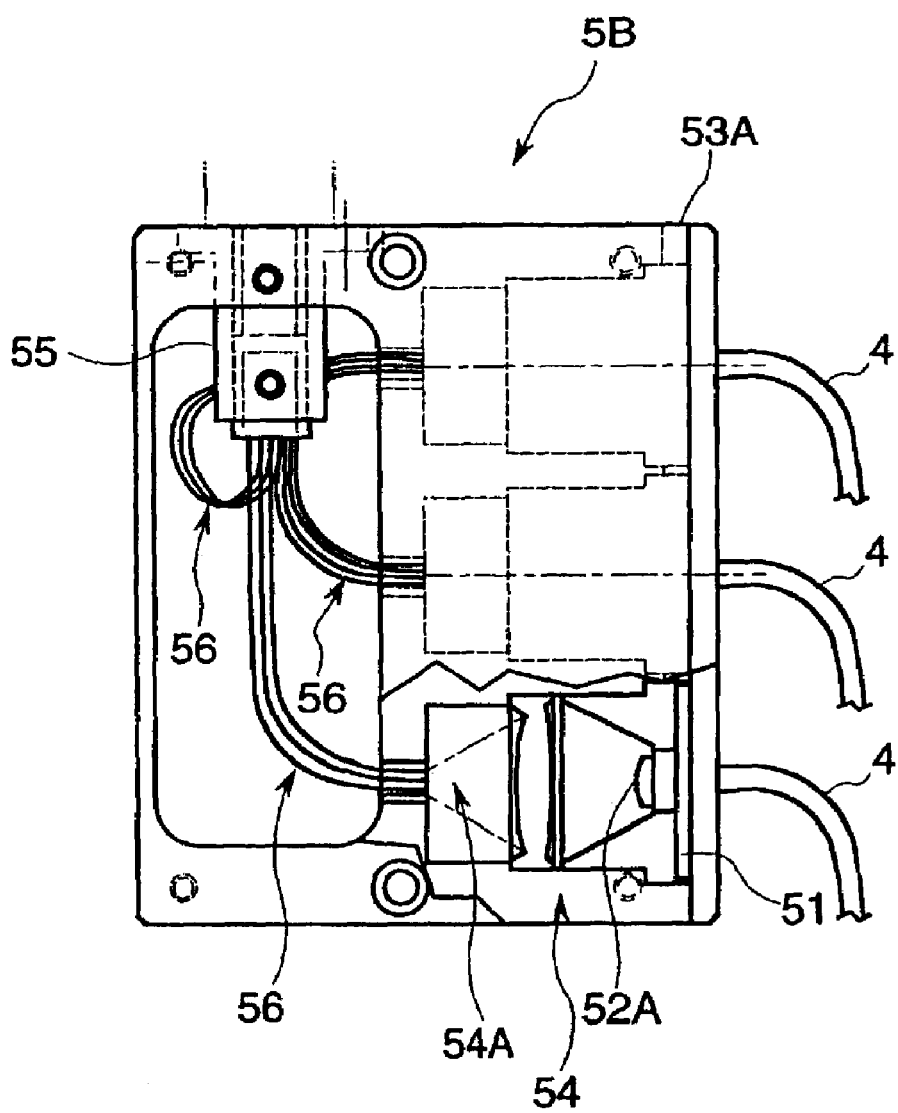
FIG. 3 is a partially cutaway front elevational view of a second LED light source device in the same embodiment.
Figure 4:
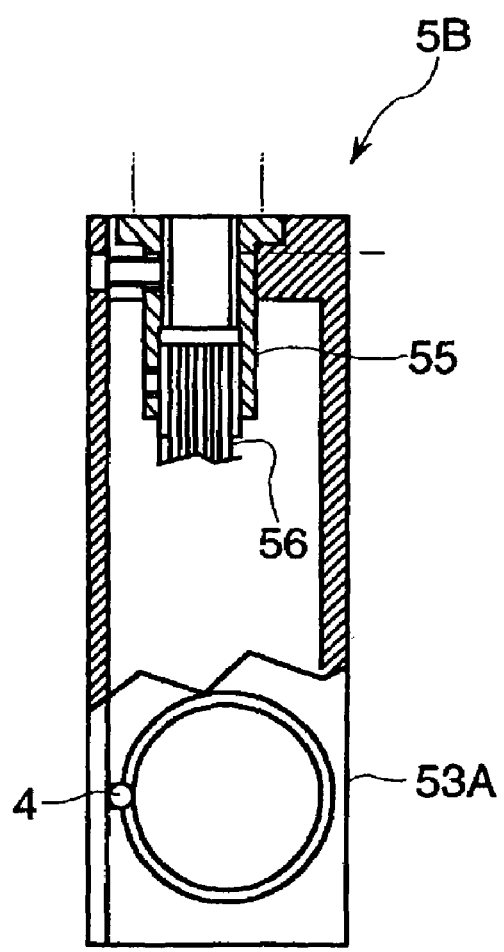
FIG. 4 is a partially cutaway side elevational view of the second LED light source device in the same embodiment.

As shown in FIGS. 3 and 4, the other LED light source device 5B comprises three LEDs 52A arranged in a row. Accordingly, the LED light source device 5B includes three substrates 51 and three lens mechanisms 54 for respective LEDs 52A. The LED light source device 5B uses only a single optical output connector 55 having a shape identical with that used in the LED light source device 5A. One end portion of an internal optical fiber bundle 56 in which end portions of respective optical fibers are tightly bundled is attached to the light-condensing portion 54a of each lens mechanism 54. The other end portion of the internal optical fiber bundle 56 in which end portions of respective optical fibers are unitarily, randomly and tightly bundled is connected to the optical output connector 55.

Figure 5:
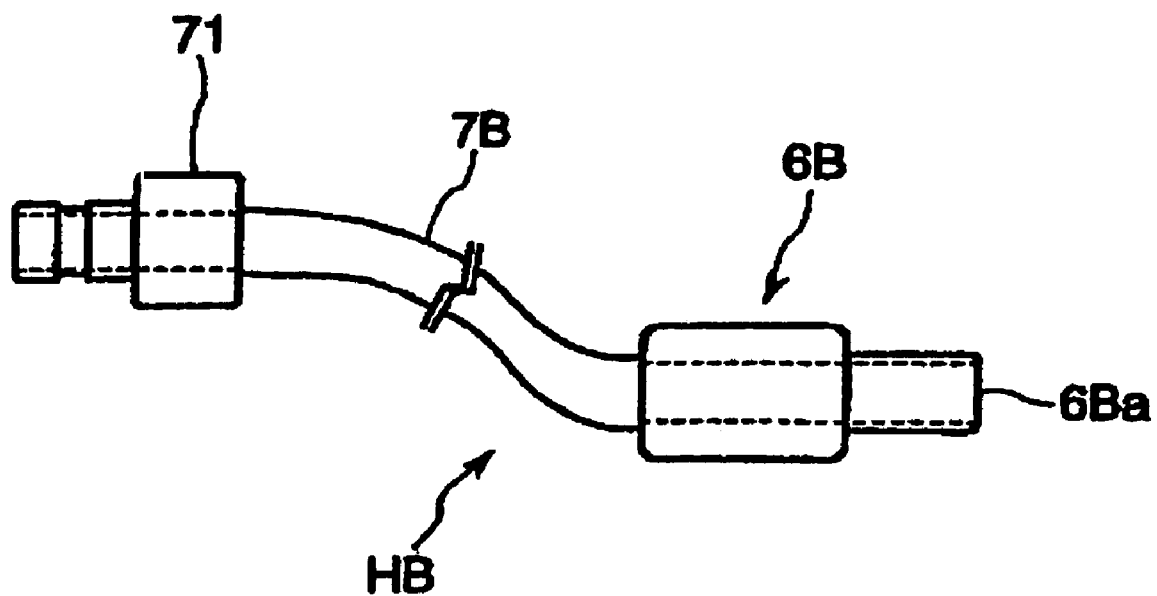
FIG. 5 is an overall view of a first head device in the same embodiment.
Figure 6:
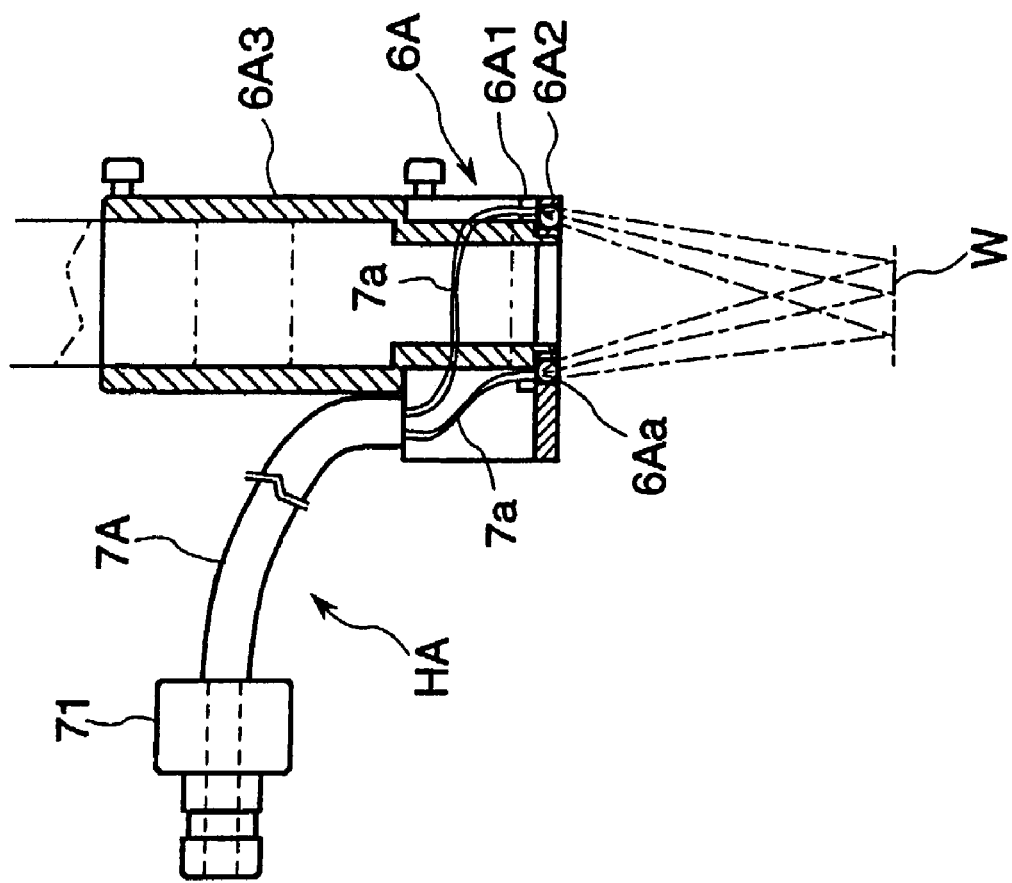
FIG. 6 is a vertical sectional view of a second head device in the same embodiment.
Figure 9:
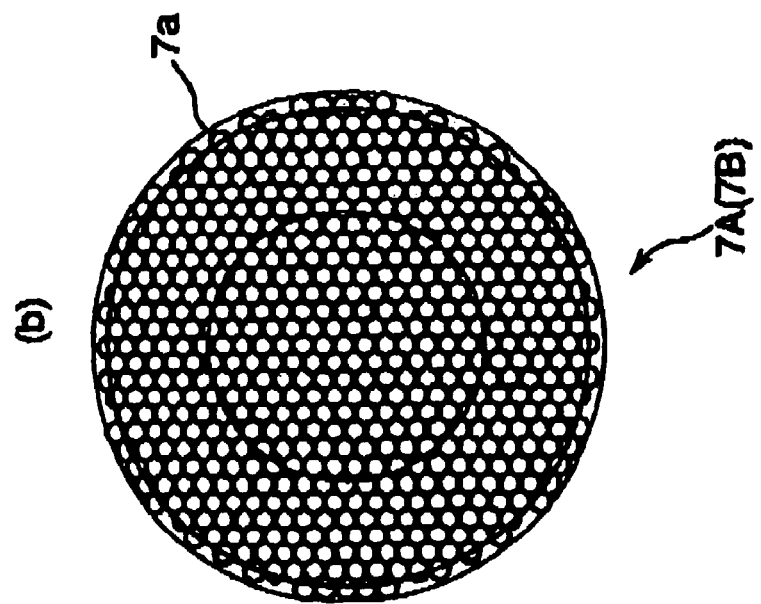
FIG. 9 is an end view illustrating a tightly bundled state of optical fibers in the same embodiment.
Figure 9:
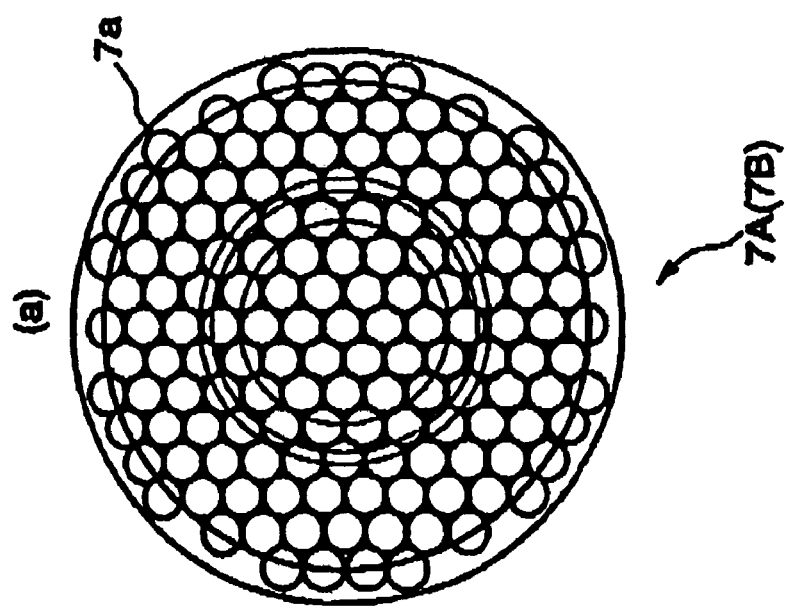

The optical fiber bundles 7A and 7B as flexible light guides sheathed with respective outer tubes extend from the LED light source devices 5A and 5B, respectively, and are exposed to the outside before connecting to respective heads 6A and 6B mounted on the unit body 2. The optical fiber bundles 7A and 7B, which are each as very short as about 30 to about 40 cm, have respective rear ends each attached to an optical input connector 71 fitted in the optical output connector 71 and respective front ends attached to respective heads 6A and 6B. The optical input connector 71, optical fiber bundle 7A (7B) and head 6A (6B) are combined to form a head device HA (HB) as shown in FIGS. 5 and 6. It is to be noted that FIG. 9 illustrates examples of the optical fiber bundle 7A (7B) comprising tightly bundled optical fibers. In this figure, optical fibers forming bundle (a) are each smaller in diameter than those forming bundle (b).

The two heads 6A and 6B, which are mounted on the unit body 2 corresponding to the two LED light source devices 5A and 5B, are each very small in size, having an outer diameter of about 10 to about 30 mm.

Figure 7:
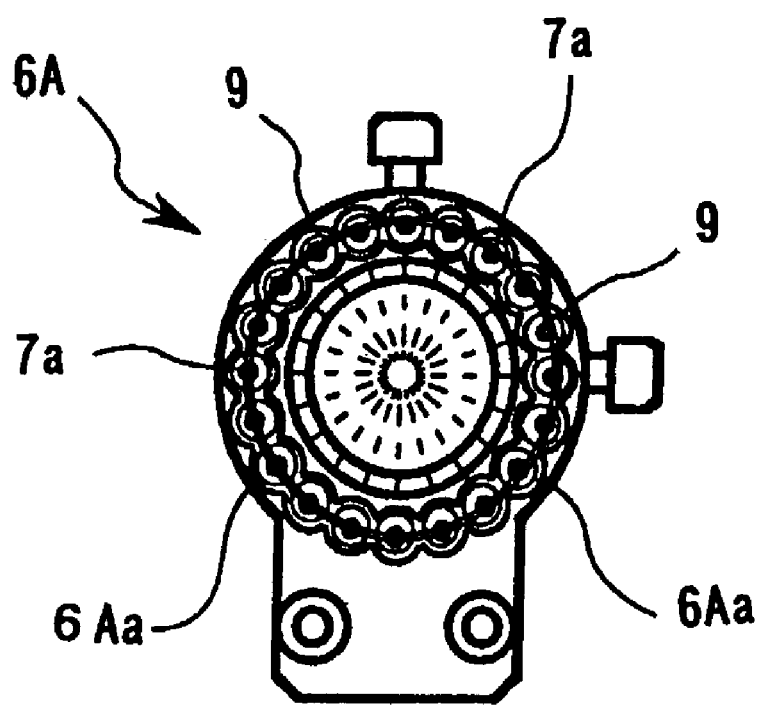
FIG. 7 is a bottom view of the second head device in the same embodiment.
Figure 8:
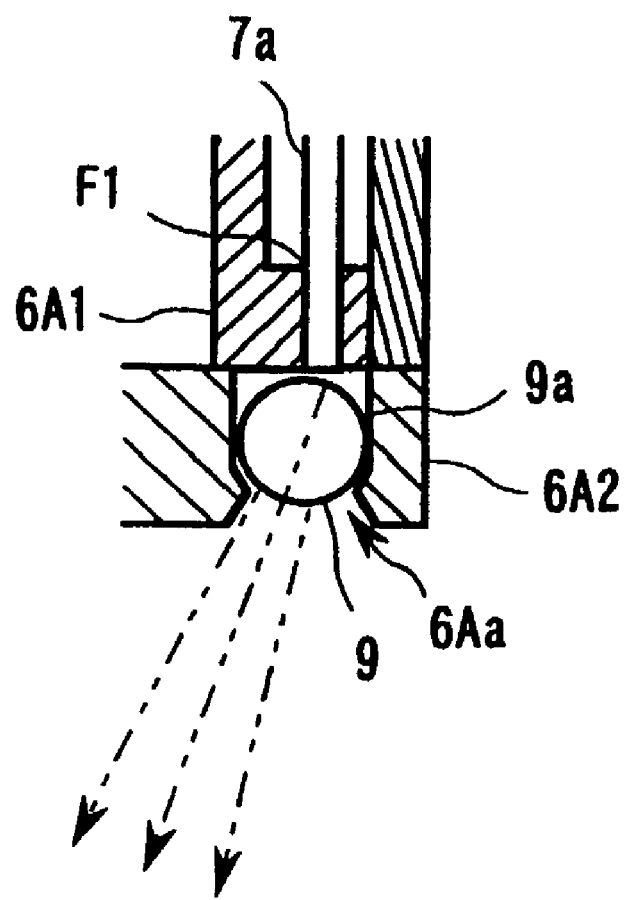
FIG. 8 is a fragmentary sectional view of the second head device in the same embodiment.

As shown in FIGS. 6 to 8, one head 6A separates front end portions of optical fibers 7a forming the front end portion of the optical fiber bundle 7A extending from the associated LED light source device 5A from each other therewithin and holds the separated front end portions as annularly arranged with spacing from each other. Specifically, the head 6A includes an annular head body 6A1 having fiber holding holes F1 equispaced and arranged annularly, the fiber holding holes F1 receiving therein respective front end portions of the optical fibers 7a to hold them, an annular lens presser plate 6A2 having ball lens holding holes 9a arranged at portions superposed on the fiber holding holes F1 to hold ball lenses 9, and a cylindrical fixture 6A3 for attaching the head 6A to the light path tube 21. The head 6A is so configured that the ball lenses 9 are brought into contact with or positioned close to respective front ends of the optical fibers 7A at a time by coaxially fixing the lens presser plate 6A2 to the head body 6A1 with a screw. As shown in FIG. 1, the head 6A is vertically slidably fitted in a lower end portion of the light path tube 22 by means of the fixture 6A3. Apertures defined under the respective ball holding holes 9a serve as illuminating apertures 6Aa for illuminating the work W positioned under the head 6A from above and around. The front end of each optical fiber 7a is attached slightly outwardly from the top of the associated ball lens 9 so that the ball lenses 9 refracts light from the optical fibers 7a to strengthen the directionality thereof while deviating light inwardly to concentrate on a portion of the work W to be illuminated.

As shown in FIG. 5, the other head 6B is of an elongated tubular shape for tightly bundling and holding front end portions of optical fibers forming the optical fiber bundle 7B extending from the associated LED light source device 5B. Light is emitted from front end faces of the tightly bundled optical fibers through a circular illuminating aperture 6Ba defined at the front end of the head 6B. As shown in FIG. 1, the head 6B is attached to an upper end portion of the light path tube 21 with its illuminating aperture 6Ba oriented in a direction perpendicular to the axis of the light path tube 21 so that light outgoing from the illuminating aperture 6a is reflected or refracted through the optical components, such as a half mirror, disposed within the light path tube 21, advances downwardly along the axis of the light path tube 21 and is emitted from a lower open end of the light path tube 21 to illuminate the work W.

The lighting unit thus constructed operates as follows.

First, when the work W such as a printed circuit board is conveyed to a predetermined position by the conveyor unit, the image pick-up device 8 reads, for example, an alignment mark of the work W, causes a non-illustrated image recognition section to recognize the mark and calculates the positional information about the mark. In turn, the XY stage 1 is automatically controlled based on the positional information so that the light path tube 21 is positioned just above a portion of the work W to be illuminated. As a result, the portion of interest is illuminated from just above and from around with light emitted from the heads 6A and 6B and the image pick-up device 8 obtains the image of the portion of interest.

In reverse, the positional information about the work W may be obtained by controlling the position of the XY stage 1 instead of reading such an alignment mark or the like. Since the positional information thus obtained can be utilized in the subsequent or later procedure, the lighting unit according to this embodiment can be utilized as a work position determining device. The lighting unit can also be utilized in reading bar codes or the like.

Since such a lighting unit allows the weights and sizes of the LED light source devices 5A and 5B to be reduced easily, the LED light source devices 5A and 5B, though mounted at the XY stage 1, can hardly exert influence on the driving of the XY stage 1, hence, of the heads 6A and 6B.

Since the electric cable 4 is far superior to an optical fiber in flexibility, durability, price and the like, the lighting unit according to the subject embodiment is capable of driving the XY stage 1 and the heads 6A and 6B with a very low burden on the electric cable as compared to the burden which has been conventionally imposed on an optical fiber when the optical fiber is moved with movements of the XY stage 1 and the heads 6A and 6B. Thus, the lighting unit exhibits superior durability and reliability.

Further, since the heads 6A and 6B are positioned at the respective front ends of the optical fiber bundles 7A and 7B, it is possible to make the sizes of the heads 6A and 6B very small as well as to condense light onto a small area. Furthermore, since the heads 6A and 6B are fixedly supported by the XY stage 1 to maintain the relative positional relation between the LED light source devices 5A and 5B and the heads 6A and 6B generally, the optical fiber bundles 7A and 7B will not deform. For this reason, destruction due to movement of the optical fiber bundles 7A and 7B can be avoided, which can eliminate the deleterious influence on the reliability, lifetime and the like of the lighting unit.

Moreover, since the subject embodiment has the feature that each of the optical fibers is attached to one lens at its front end on the head side, condensing of light can be improved substantially.

It is to be noted that the present invention is not limited to the embodiment described above and may be subject to various changes and modifications.

Figure 10:
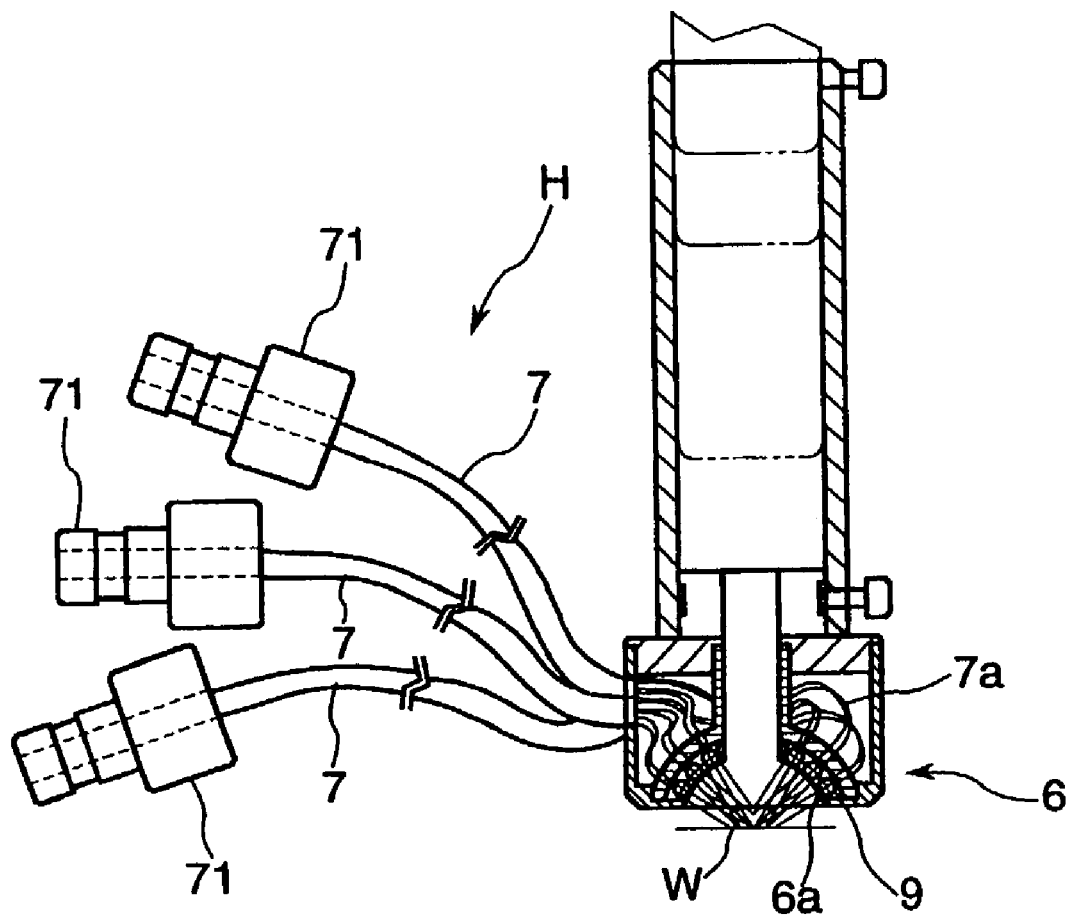
FIG. 10 is a vertical sectional view of a head device in another embodiment of the present invention.
Figure 11:
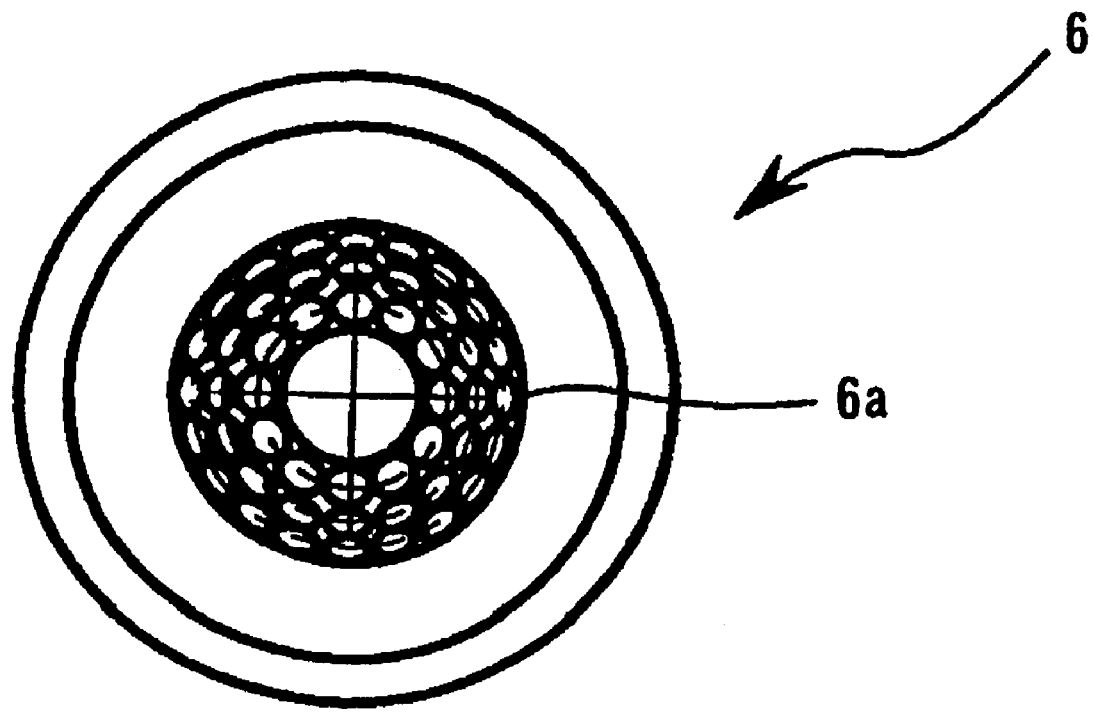
FIG. 11 is a bottom view of the head device in the same embodiment.

FIGS. 10 and 11 illustrate a head device H having a head 6 defining illuminating apertures 6a on a concave spherical surface. The illuminating apertures 6a are densely arranged on the concave spherical surface and each face a front end of each optical fiber 7a via a ball lens 9. The head device H has plural (three) optical input connectors 71 and plural (three) optical fiber bundles 7 corresponding thereto. Unlike the former embodiment, optical fibers 7a forming respective optical fiber bundles 7 are connected correspondingly to lower, middle and upper sections, whereby the lighting unit can be used for color highlight illumination. As in the former embodiment, the head device H defines a through-hole vertically extending through a central portion thereof for inspecting a work W therethrough. The optical fiber bundles 7 may be gathered randomly in the head 6.

Figure 12:
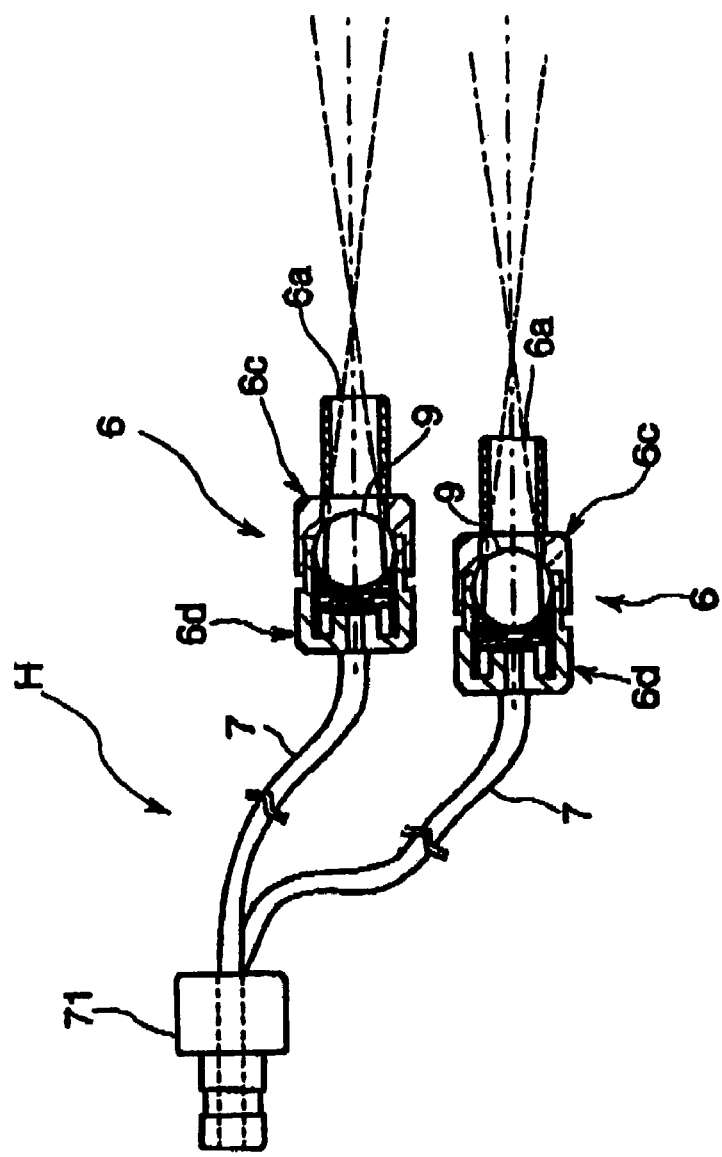
FIG. 12 is a vertical sectional view of a head device in yet another embodiment of the present invention.

FIG. 12 illustrates a head device H having plural heads 6 which are each capable of varying the spacing between a ball lens 9 and the front end of each optical fiber bundle 7 at which front ends of optical fibers are tightly bundled. These heads are each capable of varying the focal length and hence are suitable for spot lighting. Specifically, each head 6 is of a structure comprising two head elements 6c and 6d fitted with each other for making variable the spacing between the ball lens 9 and the front end of the corresponding optical fiber bundle 7 by varying the depth of the fitting between the head elements 6c and 6d. Unlike the former embodiment wherein the optical fibers are provided with the ball lenses in a one-to-one relationship, only the single ball lens is provided for each head 6.

Figure 13:
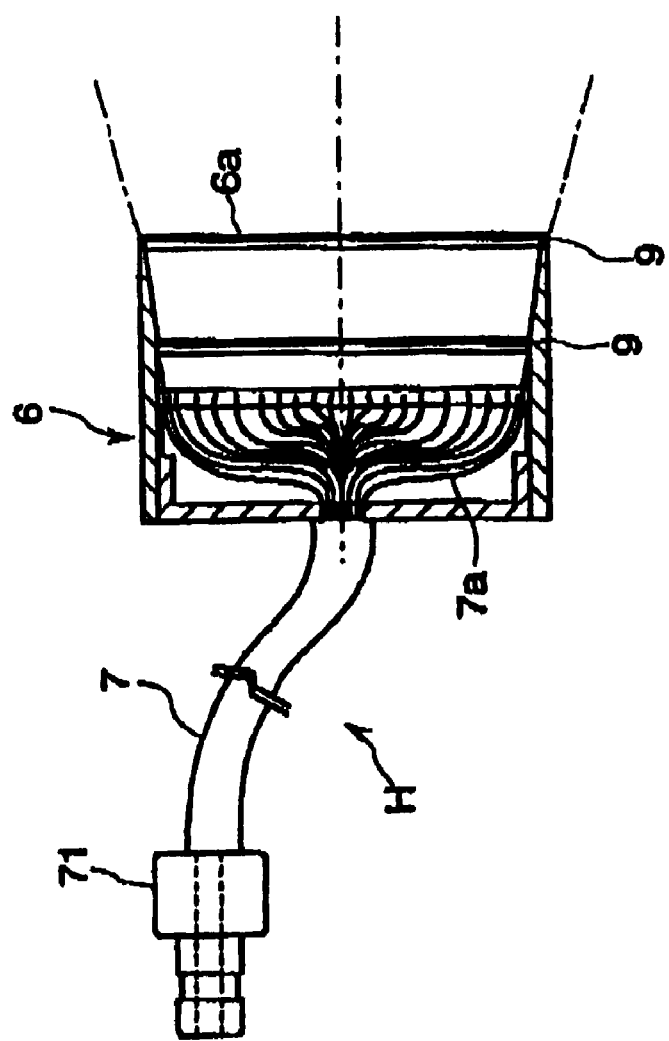
FIG. 13 is a vertical sectional view of a head device for line inspection in still another embodiment of the present invention.
Figure 14:
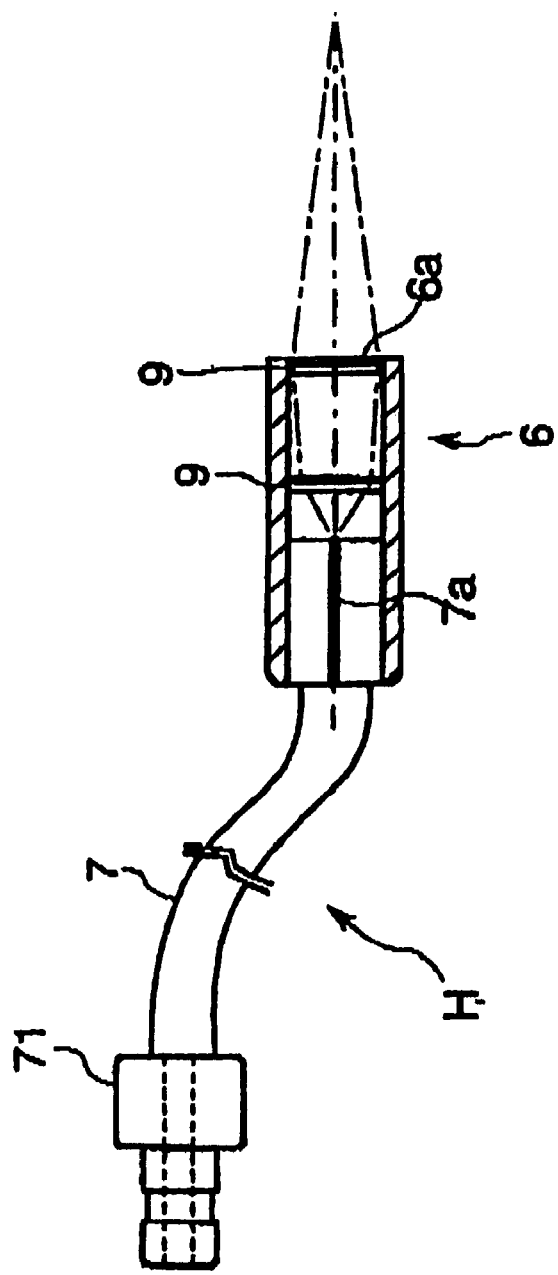
FIG. 14 is a cross sectional view of the head device in the same embodiment.
Figure 15:
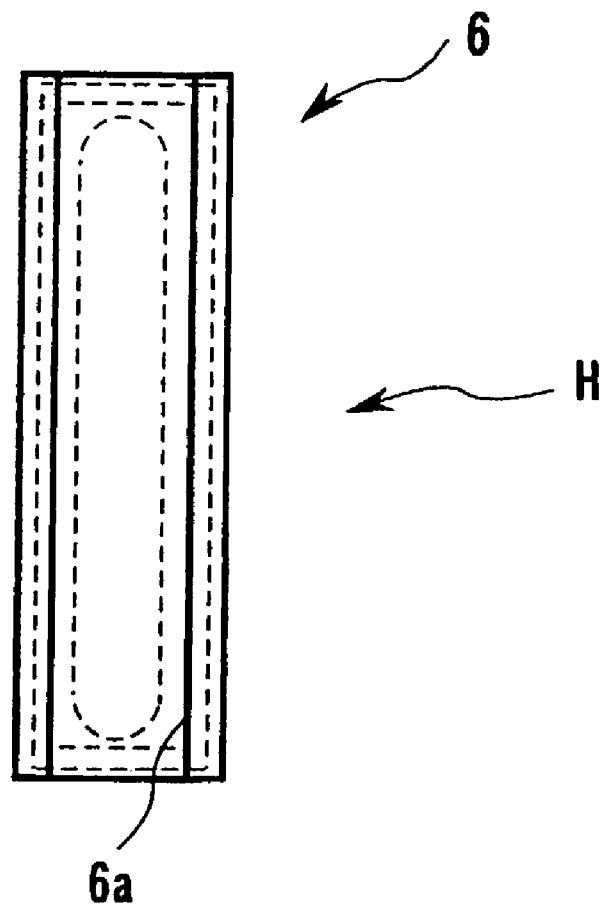
FIG. 15 is a bottom view of the head device in the same embodiment.

FIGS. 13 to 15 illustrate a head device H for use in line inspection wherein optical fibers are held with their respective front ends arranged in a single line or plural lines by a head 6. While a lens array 9 comprising linear Fresnel lenses on two stages is used for condensing light in these drawings, a cylindrical lens may be used instead of the linear Fresnel lenses.

Figure 16:
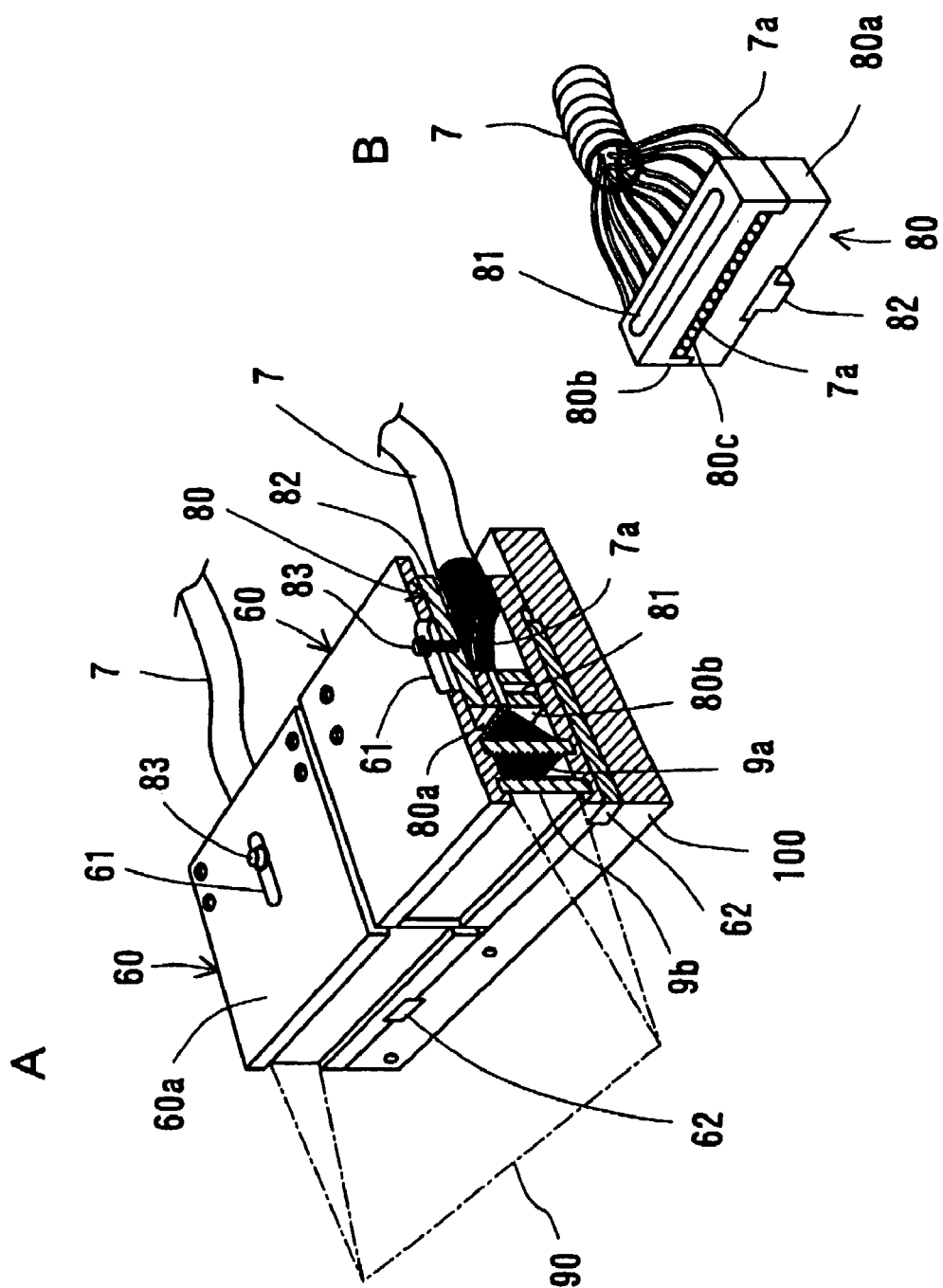
FIG. 16(A) is a partially sectional perspective view of a specific form of the head device for line inspection shown in FIGS. 13 to 15 and FIG. 16(b) is a perspective inverted view of a portion of interest of the head device.
Figure 17:
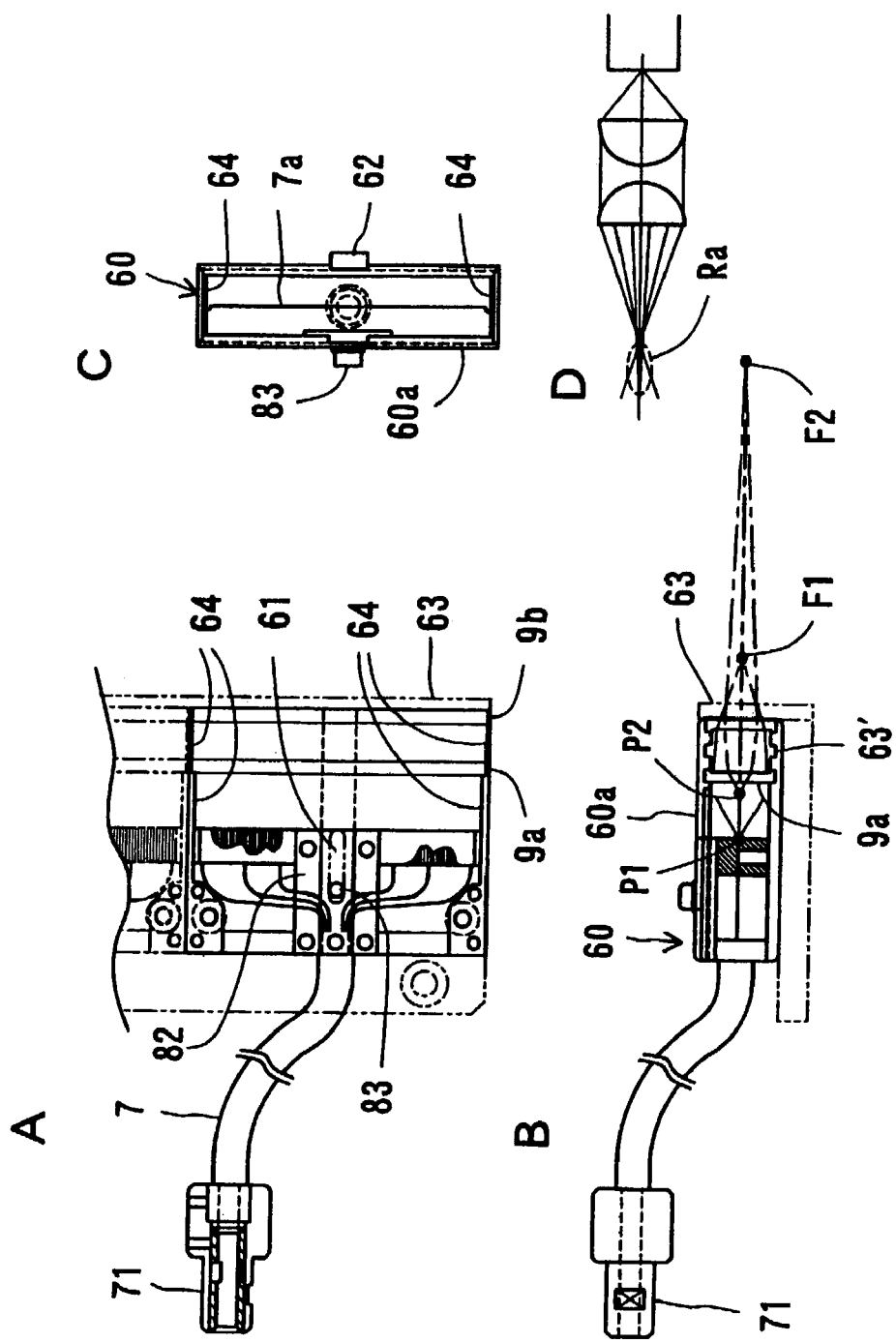
FIGS. 17(A) to 17(D) show the structure of the head device for line inspection in more detail; specifically.

FIGS. 16 and 17 illustrate a specific form of the above-described head device H for use in line inspection. FIG. 16(A) is a perspective view of the head device H including plural (two in this embodiment) head units 60 juxtaposed on a substrate 100, with the proximal head unit 60 in this view being drawn as cut vertically in half to show the internal structure thereof. FIG. 16(B) is an inverted perspective view showing a portion of interest of an optical fiber aligning and holding member. In these views, a fiber cable 7 in which a multiplicity of optical fibers 7a are bundled and accommodated extends from an optical input connector 71 serving as a light-receiving end disposed to face an light-emitting surface of a light output connector serving as an LED light source device to a rear end of each head unit 60. The front end portions of the multiplicity of optical fibers 7a are released from the bundled state within the body of the head unit 60 and are aligned and held so as to be sequentially juxtaposed with each other in a same plane by upper and lower pinch plates 80a and 80b of optical fiber aligning and holding member 80.

The front end portions of the multiplicity of optical fibers 7a are in an irregularly projecting state at the time when they are held as juxtaposed with each other between the upper and lower pinch plates 80a and 80b. Then, the front end portions of the optical fibers 7a are made flush with the front end surfaces of the pinch plates 80a and 80b. Specifically, the front end portions of the optical fibers 7a irregularly projecting from the front end surfaces of the pinch plates 80a and 80b are first cut so as to be coplanar with the front end surfaces by a hot cutter or the like, and then the cut surfaces of the optical fibers 7a are smoothed and extended by grinding or by a heat treatment using a hot plate. Thus, adjacent cut surfaces of the optical fibers 7a become substantially completely in contact and continuous with each other at the front edge (see FIG. 16B) of a fiber holding slit 80c defined by the upper and lower pinch plates 80a and 80b, thereby forming a very thin unitary light-emitting surface.

The lower pinch plate 80b is formed with an adhesive groove 81 which fixes the aligned front end portions of the multiplicity of optical fibers 7a while holding the light-emitting ends as aligned in a horizontal row in the same plane with the front end surfaces of the upper and lower pinch plates 80a and 80b. A guide portion 82 of the aligning and holding member 80 fixed on top of the upper pinch plate 80a and protruding rearward is also held in the same plane with the front end surfaces of the upper and lower pinch plates 80a and 80b. A top surface of the guide portion 82 is formed with a tapped hole which allows the fore-and-aft position of the aligning and holding member 80 to be adjusted within the range corresponding to a slot 61 defined in the head unit 60 and permits the aligning and holding member 80 to be fixed by fastening means such as a screw 83.

In a front end portion of the head unit 60 located forwardly of the fiber aligning and holding member 80, there are disposed a first lens 9a, which consists of a line Fresnel lens for example, for turning a band of light outgoing from the aligned light-emitting ends of the optical fibers 7a into parallel rays of light, and a second lens 9b, which also consists of a line Fresnel lens, for causing light outgoing from the first lens 9a to converge into a very thin line light 90, the first and second lenses 9a and 9b being spaced a predetermined distance therebetween. The head unit 60, bodily, is fixed to a base plate 100 by means of a key 62.

FIGS. 17(A) to 17(D) trigonometrically show the head device for line inspection for illustrating the structure thereof in more detail. It should be noted that the head unit 60 is shown with its top plate 60a omitted in the plan view at FIG. 17(A) and that like reference characters designate like functional parts throughout FIGS. 1 to 17. In the example shown in FIGS. 17(A) to 17(D), an optical member 63 such as a lenticular screen is provided at a front end surface of the head unit 60 for making the luminance distribution uniform in a direction in which line light extends. The optical member 63 may be positioned either between or adjacent the aforementioned pair of lenses 9a and 9b. A dent portion 63' between the lenses 9a and 9b in FIG. 17(B) is a recess for receiving the optical member 63.

Referring particularly to FIGS. 17(A) and 17(C), the opposite inner wall surfaces of the head unit 60, which extend to cover from the opposite ends of the horizontal row of light-emitting ends of optical fibers 7a to the opposite extremities of the pair of lenses 9a and 9b are each formed with a plane mirror 64 by chrome plating for example. With this feature, a loss in light quantity at the opposite ends of line light, which would otherwise result due to diffuse reflection of light diffused from the light-emitting ends of the optical fibers 7a and becoming incident on the opposite inner wall surfaces, can be compensated for by the plane mirrors 64 regularly reflecting light inwardly.

As described above, the lighting unit emitting uniform line light for line inspection shown specifically in FIGS. 16 and 17 employs the pair of lenses 9a and 9b each consisting of a line Fresnel lens or an optical component equivalent thereto. For this reason, the lighting unit is capable of providing a precise focal line forwardly of the lighting head 60 without producing an out-of-focus state essential to a cylindrical lens (cylindrical abberation similar to spherical abberation) shown as a very small range Ra in FIG. 17(D) for example. Accordingly, the lighting unit is capable of providing uniform line light having an appropriate width when an illuminated surface of an object of interest is positioned appropriately before or behind the focal line.

For example, when the light-emitting ends of the optical fibers 7a are positioned at point P1 spaced apart from the pair of lenses 9a and 9b in FIG. 17(B), the resulting focal line is positioned at point F1 relatively close to the front end of the lighting head 60. In contrast, when the light-emitting ends of the optical fibers 7a are positioned at point P2 closer to the pair of lenses 9a and 9b in FIG. 17(B), the resulting focal line is positioned at point F2 relatively apart from the front end of the lighting head 60, thereby providing thinner line light. In this way the focal length of the lighting unit can be adjusted as desired in inspection.

As shown in FIG. 17, the opposite sidewalls of the head unit 60 are each very thin as compared with the width of the horizontal row of optical fibers 7a and, hence, the length of line light at a required illuminating position is equal to or slightly larger than the width of the head unit. By arranging a plurality of such head units in a row, it is possible to form a uniform line light illumination pattern having a length corresponding to the total width of these head units.

The uniform line light illumination thus realized is capable of showing a surface illuminated with continuous and elongated line light having a relatively high luminance. For this reason, even when very minute roughness exists in the illuminated surface, such roughness is shown as a variation in the reflection of illuminating light, thus making precise optical observation possible. Particularly, the drawback of the prior art that a variation in luminance occurs for each optical fiber to cause discontinuity of brightness to result can be overcome by making the luminance distribution uniform with use of the lenticular screen. The use of the line Fresnel lens for condensing light prevents light from diffusing unnecessarily for the line sensor and hence makes it possible to reduce the power consumption. For this reason, the line light-emitting lighting unit can be preferably used in lighting for inspection of printed circuit boards and pin grid arrays in particular.

Figure 18:
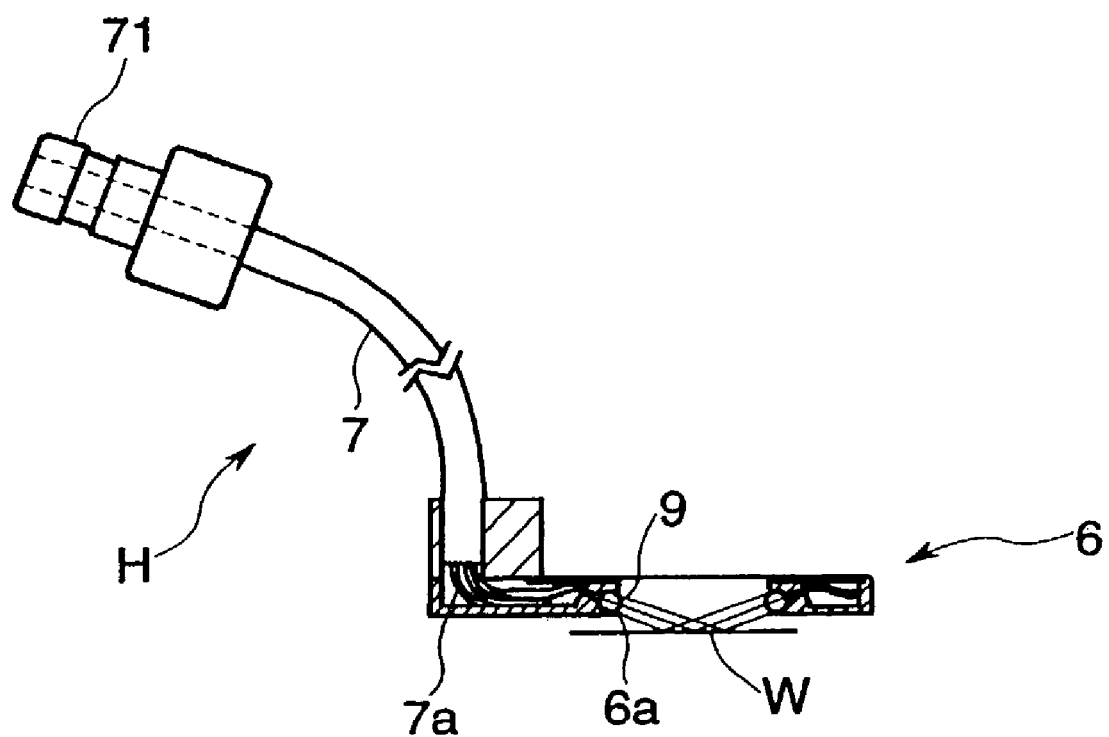
FIG. 18 is a vertical sectional view of a head device in still another embodiment of the present invention.

FIG. 18 shows a head device H of a ring type similar to the foregoing embodiment. The head device H has a thin head 6 and hence is suitable for use in applications where the distance between a work W and the illuminating aperture 6a is short, such as a microscope.

Of course, variations of other components than the head are conceivable. Since the length and weight of the optical fibers can be reduced if the LED light source devices are disposed adjacent the respective illuminating apertures, the heads can be driven smoothly even when they are movably supported on the XY stage. In this case, it is preferred that the heads be made movable slightly or slowly relative to the XY stage unless a problem arises in relation to the reliability, lifetime and the like of the optical fibers.

The lighting unit of the present invention can be constructed using a single optical fiber instead of using an optical fiber bundle. It is also possible that a battery is incorporated in or incident to each LED light source device as an electric power source. By so doing, the lighting unit can be rendered cableless. Alternatively, such an arrangement is possible that the LED light source devices are supplied with electric power from any other mechanism forming part of the lighting unit of the present invention than the electric power source such as the image pick-up device or the driving mechanism associated with the XY stage.

The movable support member is not limited to the XY stage and may be any one of various movable support members including one capable of three-dimensional positioning.

If full-color lighting is performed using LEDs emitting light of plural colors (three colors), it is preferable that optical fibers for emitting lights of respective colors are arranged homogeneously on the head 6A, 6B side.

As has been described in detail, the present invention makes it possible to reduce the weight and size of the LED light source device easily and, therefore, the LED light source device thus reduced in weight and size, though mounted at the movable support member, can hardly exert influence on the driving of the movable support member, hence, of the head.

If the head is fixedly supported by the movable support to maintain the relative positional relation between the LED light source device and the head, it is possible to reduce the burden to be imposed on the optical fiber, thereby to eliminate the influence of such a burden on the reliability, lifetime and the like of the optical fiber. Of course, the head may be mounted at the movable support member so as to be slightly movable or slowly movable unless such movement affects the reliability, lifetime and the like of the optical fiber.

Since the head is connected to the optical fiber and is separate from the LED light source device, it is possible to make the size of the head very small as well as to condense light onto a small area. Further, since the light source can be spaced apart to a certain extent from the object to be illuminated or from the image pick-up device for imaging the object, it is also possible to prevent the object or the image pick-up device from being affected by heat generated from the light source.

The LED light source device may be supplied with electric power either from a battery provided in or incident to the lighting unit or from an electric power source disposed separately from the movable support member through an electric cable. With the former arrangement, the lighting unit can be rendered cableless. Alternatively, though the latter arrangement requires an electric cable, the electric cable is far superior to an optical fiber in flexibility, durability, price and the like. The latter arrangement is capable of highly reliably driving the movable support member and the head with a very light burden on the electric cable as compared to the burden that has been conventionally imposed on an optical fiber when the optical fiber is moved with the movement of the head. An arrangement for supplying electric power from the image pick-up device may also be conceived.

In the present invention, the light source device may be disposed adjacent the illuminating aperture to shorten the optical fiber (to 1 m or less for example), thereby reducing the weight of the optical fiber. With this feature, the head can be driven smoothly even if it is movably mounted at the movable support member. In this case, it is preferred that the head be mounted at the movable support member so as to be slightly movable or slowly movable relative to the movable support member unless such movement affects the reliability, lifetime and the like of the optical fiber.

While only certain presently preferred embodiments of the present invention have been described in detail, as will be apparent for those skilled in the art, certain changes and modifications may be made in embodiments without departing from the spirit and scope of the present invention as defined by the following claims.

What is claimed is:

1. A lighting unit comprising:
   a head, an LED light source, and a multiplicity of optical fibers; where
   the multiplicity of optical fibers, the LED light source, and the head are all supported by a movable support member;
   the head and LED light source are fixed in position relative to each other;
   the head defines an illuminating aperture for directing light to an object to be illuminated; and
   the multiplicity of flexible optical fibers guide light from the LED light source to the illuminating aperture of the head.

2. The lighting unit according to claim 1, wherein the LED light source device is supplied with electric power from an electric power source disposed separately from the movable support member through an electric cable.

3. The lighting unit according to claim 1, wherein the light source device is disposed adjacent the illuminating aperture.

4. The lighting unit according to claim 1, wherein the optical fiber is fitted with a lens at a front end thereof on a head side.

5. A lighting unit comprising:
   a head unit;
   an LED light source device external to the head unit;
   a multiplicity of optical fibers extending from light-receiving ends thereof facing a light emitting surface of an LED light source device into the head unit;
   a fiber cable in which optical fibers are bundled and accommodated;
   an optical fiber aligning and holding member consisting of upper and lower pinch plates holding light-emitting ends of the respective optical fibers in direct contact with each other and aligned in a horizontal row by releasing the bundled state of front end portions of the multiplicity of optical fibers introduced into the head unit from a rear end thereof within the head unit and sequentially juxtaposing the front end portions with each other in a same plane; and a pair of lenses fitted at a front end portion of the head unit, the pair of lenses consisting of a first lens for turning a band of light emitted from the horizontal row of the light-emitting ends of the optical fibers into substantially parallel rays of light and a second lens for causing light outgoing from the first lens to converge into line light consisting of an elongated band of light.

6. The lighting unit according to claim 5, wherein the optical fiber aligning and holding member is mounted at the head unit so as to be position-adjustable in fore-and-aft directions.

7. The lighting unit according to claim 5, further comprising an optical member for providing a uniform luminance distribution in a direction in which the line light extends, the optical member being disposed at the front end portion of the head unit so as to be associated with the pair of lenses.

8. The lighting unit according to claim 5, wherein the head unit has opposite inner wall surfaces formed with respective plane mirrors extending to cover from opposite ends of the horizontal row of the light-emitting ends of the multiplicity of optical fibers to opposite extremities of the pair of lenses.

9. A lighting unit comprising a plurality of lighting units as recited in claim 5 with respective head units arranged in a row for forming a continuous line light illumination pattern having a length corresponding to a total width of the head units.

10. A lighting unit comprising:
a head unit;
an LED light source device external to the head unit;
a multiplicity of optical fibers extending from light-receiving ends facing a light-emitting surface of the LED light source device into the head unit;
a fiber cable in which the optical fibers are bundled and accommodated;
an optical fiber aligning and holding member holding light-emitting ends of the respective optical fibers as aligned in a horizontal row by releasing the bundled state of front end portions of the multiplicity of optical fibers introduced into the head unit from a rear end thereof within the head unit and sequentially juxtaposing the front end portions with each other in a same plane, the optical fiber aligning and holding member being position-adjustable in fore-and-aft directions within the head unit;
converging and illuminating means provided at a front end portion of the head unit for causing a band of light emitted from the horizontal row of the light-emitting ends of the optical fibers to converge into a thinner band of light at a position forward of the head unit;
a lenticular screen for providing a uniform luminance distribution in a direction in which line light extends, the lenticular screen being disposed at the front end portion of the head unit so as to be associated with the converging and illuminating means; and
a pair of plane mirrors formed on opposite inner wall surfaces of the head unit so as to extend to cover from opposite ends of the horizontal row of the light-emitting ends of the multiplicity of optical fibers to opposite extremities of the converging and illuminating means.

11. A lighting unit comprising a fiber cable extending between a head unit and an LED light source external to the head unit, the cable having a multiplicity of optical fibers extending the length of the cable, the fibers having light-receiving ends facing a light-emitting surface of the LED light source and light-emitting ends extending into the head unit, wherein the head unit comprises:
an optical fiber aligning and holding member that aligns the light-emitting ends of the optical fibers in a horizontal row by sequentially juxtaposing the light emitting portions with each other in a plane, and that is position-adjustable in fore-and-aft directions within the head unit;
converging and illuminating means provided at a front end portion of the head unit for causing a band of light emitted from the horizontal row of the light-emitting ends of the optical fibers to converge into a thinner band of light at a position forward of the head unit;
a lenticular screen for providing a uniform luminance distribution in a direction in which the thinner band of light extends, the lenticular screen being disposed at the front end portion of the head unit so as to be associated with the converging and illuminating means; and
a pair of plane mirrors formed on opposite inner wall surfaces of the head unit so as to extend to cover from opposite ends of the horizontal row of the light-emitting ends of the multiplicity of optical fibers to opposite extremities of the converging and illuminating means.

12. A lighting unit comprising:
a movable support member;
a head defining an illuminating aperture for directing light to an object to be illuminated, the head being supported by the movable support member;
an LED light source device supported by the movable support member; and
a multiplicity of flexible optical fibers for guiding light from the LED light source device to the illuminating aperture of the head; wherein
movement of the movable support member causes movement of the head and LED light source device but does not cause a change in distance between the head and the LED light source device.

13. The lighting unit of claim 12 further comprising a power cable providing power to the LED light source device wherein movement of the movable support member does not cause the multiplicity of flexible optical fibers to flex, but does cause the power cable to flex.

* * * * *